(12) United States Patent
Hoefel et al.

(10) Patent No.: US 8,073,503 B2
(45) Date of Patent: Dec. 6, 2011

(54) PERSONAL HEALTH MODULES SUPPORTED BY PORTABLE COMMUNICATION DEVICES

(75) Inventors: Guilherme Luiz Karnas Hoefel, San Diego, CA (US); Liren Chen, San Diego, CA (US); Jack Steenstra, San Diego, CA (US); Kirk S. Taylor, San Diego, CA (US); Yang Zhang, San Diego, CA (US)

(73) Assignee: Qualcomm Incorporated, San Diego, CA (US)

( * ) Notice: Subject to any disclaimer, the term of this patent is extended or adjusted under 35 U.S.C. 154(b) by 895 days.

(21) Appl. No.: 11/935,644

(22) Filed: Nov. 6, 2007

(65) Prior Publication Data

US 2009/0117861 A1 May 7, 2009

(51) Int. Cl.
*H04M 1/00* (2006.01)

(52) U.S. Cl. ............ 455/575.1; 455/90.3; 455/128; 455/106; 714/22; 174/370

(58) Field of Classification Search .......... 455/575.1, 455/90.3, 128, 106, 300, 301, 575.5, 3.06; 714/22; 174/370, 388
See application file for complete search history.

(56) References Cited

U.S. PATENT DOCUMENTS

| | | | | |
|---|---|---|---|---|
| 5,944,659 | A * | 8/1999 | Flach et al. | 600/300 |
| 6,008,980 | A * | 12/1999 | Stevenson et al. | 361/302 |
| 6,159,424 | A | 12/2000 | Kauhaniemi et al. | |
| 6,295,506 | B1 | 9/2001 | Heinonen et al. | |
| 6,485,416 | B1 | 11/2002 | Platt et al. | |
| 7,005,573 | B2 * | 2/2006 | Lionetta et al. | 174/387 |
| 7,031,745 | B2 | 4/2006 | Shen | |
| 7,326,862 | B2 * | 2/2008 | Lionetta et al. | 174/370 |
| 7,347,836 | B2 | 3/2008 | Peterson et al. | |
| 7,490,266 | B2 * | 2/2009 | May | 714/22 |
| 7,611,358 | B2 * | 11/2009 | Cox et al. | 439/65 |
| 7,835,694 | B2 * | 11/2010 | Shiff | 455/13.1 |
| 2001/0023315 | A1 * | 9/2001 | Flach et al. | 600/300 |
| 2001/0050837 | A1 * | 12/2001 | Stevenson et al. | 361/306.1 |
| 2004/0117212 | A1 | 6/2004 | Kong et al. | |
| 2004/0165369 | A1 * | 8/2004 | Lionetta et al. | 361/818 |

(Continued)

FOREIGN PATENT DOCUMENTS

DE 2005028203 9/2006

(Continued)

OTHER PUBLICATIONS

European Search Report—EP10177389—Search Authority—Munich—Apr. 8, 2011.
International Search Report and Written Opinion—PCT/US2008/082665, International Search Authority—European Patent Office—Sep. 11, 2009.

*Primary Examiner* — Minh D Dao
(74) *Attorney, Agent, or Firm* — James T. Hagler (57) ABSTRACT

A wireless device having a remote station portion, such as a cellular telephone, PDA, laptop computer, handheld computer, or the like and a removably connectable medical device portion, such as a blood glucose monitor or the like, is provided. The medical device portion is separated from the remote station portion by an isolation circuit and electromagnetic shielding to inhibit the electronics and radio frequency transmission of the remote station portion interfering with the medical device. Moreover, a control processor in the remote station portion has a battery management module to disable functions as the charge in the power source falls to provide sufficient power for operation of the medical device.

15 Claims, 5 Drawing Sheets

U.S. PATENT DOCUMENTS

| | | |
|---|---|---|
| 2005/0019848 A1 | 1/2005 | Lee et al. |
| 2006/0040171 A1 | 2/2006 | Lee |
| 2006/0081469 A1 | 4/2006 | Lee |
| 2006/0110599 A1* | 5/2006 | Honma et al. ................. 428/413 |
| 2006/0229503 A1 | 10/2006 | Fluegel |
| 2007/0177771 A1 | 8/2007 | Tanaka et al. |
| 2007/0270918 A1* | 11/2007 | De Bel et al. .................... 607/48 |
| 2008/0220814 A1 | 9/2008 | Hedtke et al. |
| 2009/0243756 A1* | 10/2009 | Stevenson et al. ............ 333/172 |
| 2010/0286744 A1* | 11/2010 | Echt et al. ....................... 607/32 |

FOREIGN PATENT DOCUMENTS

| | | |
|---|---|---|
| EP | 1722310 A1 | 11/2006 |
| JP | 2006102388 | 4/2006 |
| WO | 2005/079664 | 9/2005 |
| WO | 2006/092323 | 9/2006 |

* cited by examiner

PERSONAL HEALTH MODULES SUPPORTED BY PORTABLE COMMUNICATION DEVICES

CLAIM OF PRIORITY UNDER 35 U.S.C. §119

None.

CLAIM OF PRIORITY UNDER 35 U.S.C. §120

None.

REFERENCE TO CO-PENDING APPLICATIONS FOR PATENT

None.

BACKGROUND

1. Field

The technology of the present application applies to personal health module supported by a portable communication device, and more specifically to a personal health module removably mounted to a portable communication device where the portable communication device provides priority to the personal health module and shielding between the portable communication device and personal health module.

2. Background

Portable communication devices, such as radios and cellular telephones are useful devices in everyday operations. Some personal health electronics, such as, for example, blood glucose monitors, include radio frequency communication capability to transmit personal health information from the monitor to a central repository of data.

Incorporating the personal health electronics, which for clarity will be generally referred to as a personal health module, into an existing radio frequency communication unit, such as, for example, a conventional cellular telephone, would be desirous except that integrating the functionality of a personal health module, which may include medical equipment, into a generic radio frequency communication unit, such as a cellular telephone, may convert the generic radio frequency communication unit to a medical device subject to the requirements of the food and drug administration for medical devices. Moreover, the radio transmitter or other electronics associated with portable communication device, in some cases, may impact the functionality of the integrated personal health module.

Thus, it would be desirous to provide a conventional portable communication device that is capable of being integrated with a personally health module such that the conventional portable communication device is not considered a medical device and the portable communication device does not interfere or influence the functionality of the personal health module.

SUMMARY

Embodiments disclosed herein address the above stated needs by providing a wireless device that integrates a personal health module with a portable communication device remote station. Aspects of the technology of the present application include a wireless device. The wireless device has a portable communication device contained in a housing adapted to receive/house a personal health module. The portable communication device comprises a control processor that controls the functions of at least the portable communication device. The portable communication device includes a user interface connected to the control processor to allow a user to interact with at least the portable communication device and, as explained below, potentially the personal health module. A personal health module is mechanically connected and housed with the portable communication device and electrically connected to the portable communication device through an isolation circuit. The isolation circuit electrically isolates the personal health module from the portable communication device. Shielding is provided between the portable communication device and the personal health module to inhibit interference with the personal health module. The shielding, as explained below, may be electromagnetic shielding to inhibit the radio frequency transmissions from interfering with the personal health module. The shielding, as explained below, may be heat shielding to reduce the impact of heat generation from interfering with the personal health module. The shielding, as explained below, may be moisture shielding to reduce the impact of moisture from interfering with the personal health module. The shielding, as explained below, may be a hermetic to reduce the impact of environmental factors from interfering with the personal health module. The shielding, as explained below, may include an antibacterial/microbial component to reduce the impact of biologics from interfering with the personal health module and/or inhibit the spread of infection. The shielding may be one or a combination of these and other types of shielding.

Other aspects of the technology of the present invention include methods for managing power consumption in a wireless device having a portable communication device and a personal health module. The method includes monitoring a charge on a power source of the wireless device and determining whether the charge for the power source decreases below a first predetermined threshold. If the charge is below the first predetermined threshold, signaling the control processor that the charge for the power source has decreased below the first predetermined threshold; and disabling components of the wireless device to reduce power consumption.

DETAILED DESCRIPTION

The technology of the present invention will now be described with particular reference to the figures. While the technology is described with particular reference to cellular telephones as the portable communication device, one of ordinary skill in the art of the technology described will now recognize on reading the disclosure herein that the technology of the present application may be implemented in any wireless (or wired) device including, for example, cellular telephones, desktop computers, laptop computers, handheld computers, electronic games, portable digital assistants, MP3 players, DVD players, or the like. Additionally, the personal health modules discussed below may be incorporated into multiple traditionally mobile devices or multiple traditionally non-mobile devices.

The technology of the present application is described with reference to specific exemplary embodiments. The word "exemplary" is used herein to mean "serving as an example, instance, or illustration." Any embodiment described herein as "exemplary" is not necessarily to be construed as preferred or advantageous over other embodiments. Additionally, all embodiments described herein should be considered exemplary unless otherwise stated.

The word "network" is used herein to mean one or more conventional or proprietary networks using an appropriate network data transmission protocol. Examples of such networks includes, PSTN, LAN, WAN, WiFi, WiMax, Internet, World Wide Web, Ethernet, other wireless networks, and the like.

Figure 1:
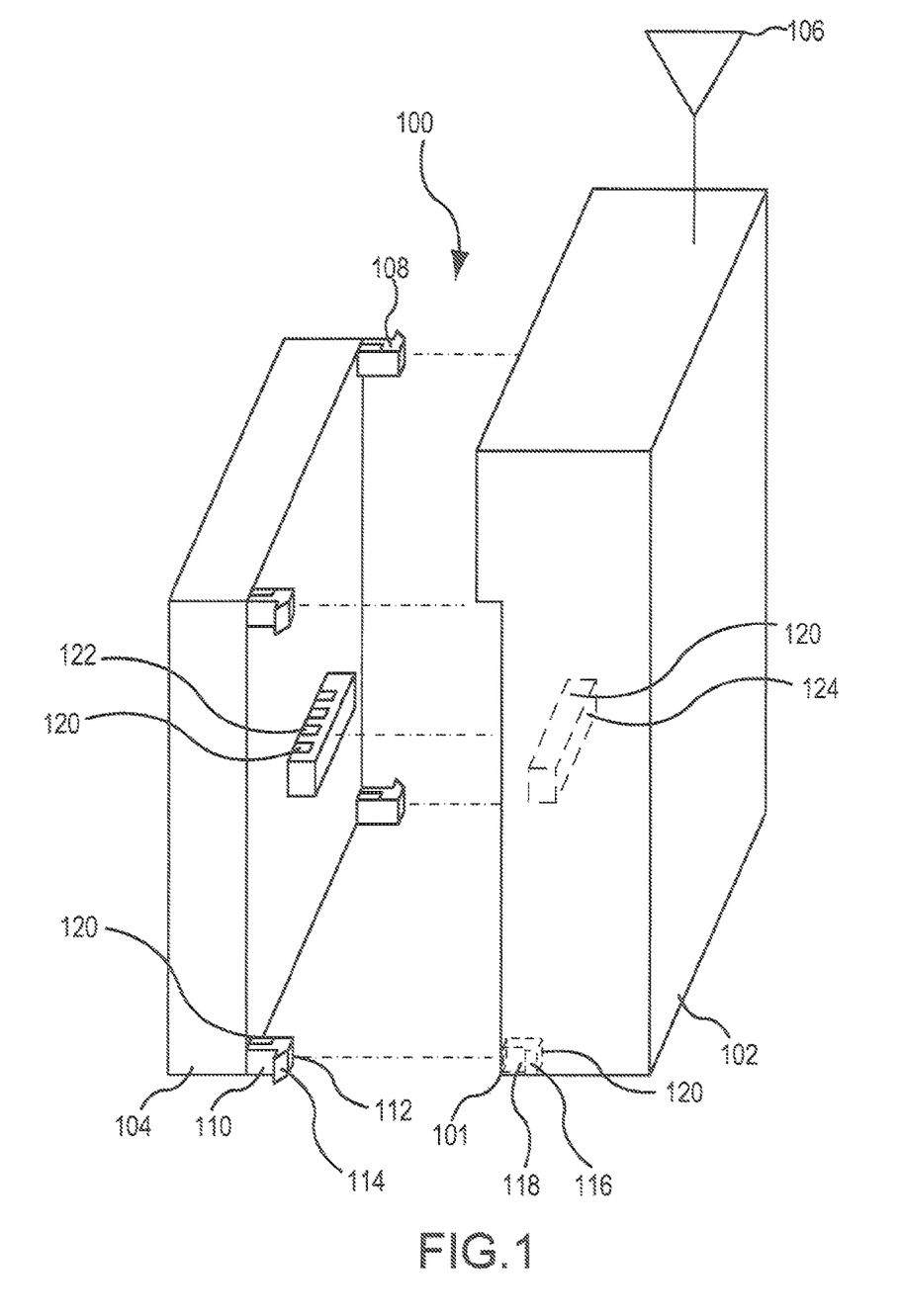
FIG. 1 is a partially exploded perspective view of a wireless device of an exemplary embodiment.

Referring first to FIG. 1, a wireless device 100 constructed using the technology of the present application is illustrated. In this exemplary wireless device 100, wireless device 100 includes a portable communication device 102 and a personal health module 104. Wireless device 100 is shown partially exploded for convenience. Portable communication device 102 would have at least one radio frequency antenna 106, but may have multiple antennas. Frequently, portable communication device 102 will transmit and receive radio frequency signals over multiple operational frequencies that may require either multiple antennas or a single antenna that operates over the necessary frequencies. Portable communication device 102 may consist of any number of devices such as, for example, a wireless computer, a portable digital assistant (such as a BLACKBERRY®, from Research in Motion, Ltd), a cellular telephone, or the like. Although shown and described as a portable communication device, one of ordinary skill in the art on reading the present application will now recognize that wireless device 100 may be a wired (or a traditionally non-portable) device including a conventional computing device that is connected to a network via a conventional modem, ISP, or the like via a wired connection. For example, instead of a portable communication device wireless device 100 may comprise a desktop computer and personal health module 104.

Wireless device 100 as explained above also has one or more personal health modules (PHMs) 104, although only one PHM 104 is shown for convenience. Optionally, portable communication device 102 has a recess 101 to accommodate PHM 104 such that wireless device 100 houses both portable communication device 102 and PHM 104. PHMs 104 may include, by way of non-limiting example, a pulse meter, a blood glucose meter, a oxygen meter, a cardio monitor etc. PHMs 104 may be integrated into wireless device 100 or removably connectable to wireless device 100 as a plug-in module or the like. PHM 104 shown in FIG. 1 is removably coupled to wireless device 100 by, for example, a plurality of connections 108, which are shown as snap fit connection 108. As shown snap fit connection 108 includes a protrusion 110 extending from PHM 104 with a flared end 112 forming lip 114. Protrusion 110 and flared end 112 fit into a corresponding socket 116 in wireless device 100 having a shoulder 118. Protrusion 110 should be flexible to allow flared end 112 to pass shoulder 118 such that lip 114 and shoulder 118 abut to mechanically couple or snap fit PHM 104 to portable communication device 102. Electrical connection could be by conductive traces 120 on the snap fitting or a separate tab 122 with conductive traces 120 fitting into a slot 124 with corresponding conductive traces 120. Electrical and mechanical coupling of PHM 104 to portable communication device 102 should be arranged such that the electrical connection and mechanical connections facilitate connecting a plurality of PHMs 104 to a plurality of portable communication devices 102. Thus, for example, portable communication device 102 may couple (electrically and mechanically) to a first blood glucose meter PHM 104 and a second cardio meter PHM 104. Moreover, for example, first blood glucose meter PHM 104 may couple (electrically and mechanically) to a cellular telephone portable communication device 102 or a personal computer portable communication device 102.

Wireless device 100 is described generally as a compact device for mobility, but one of ordinary skill in the art will recognize that wireless device 100 also may be a special processor uniquely designed for the above system, a desktop computer, a laptop computer, a handheld computer, as well as other processors as described above. Moreover, wireless device 100 is not required to be a wireless device, however, it is envisioned that the technology of the present application would be more applicable to wireless, mobile devices.

Figure 2:
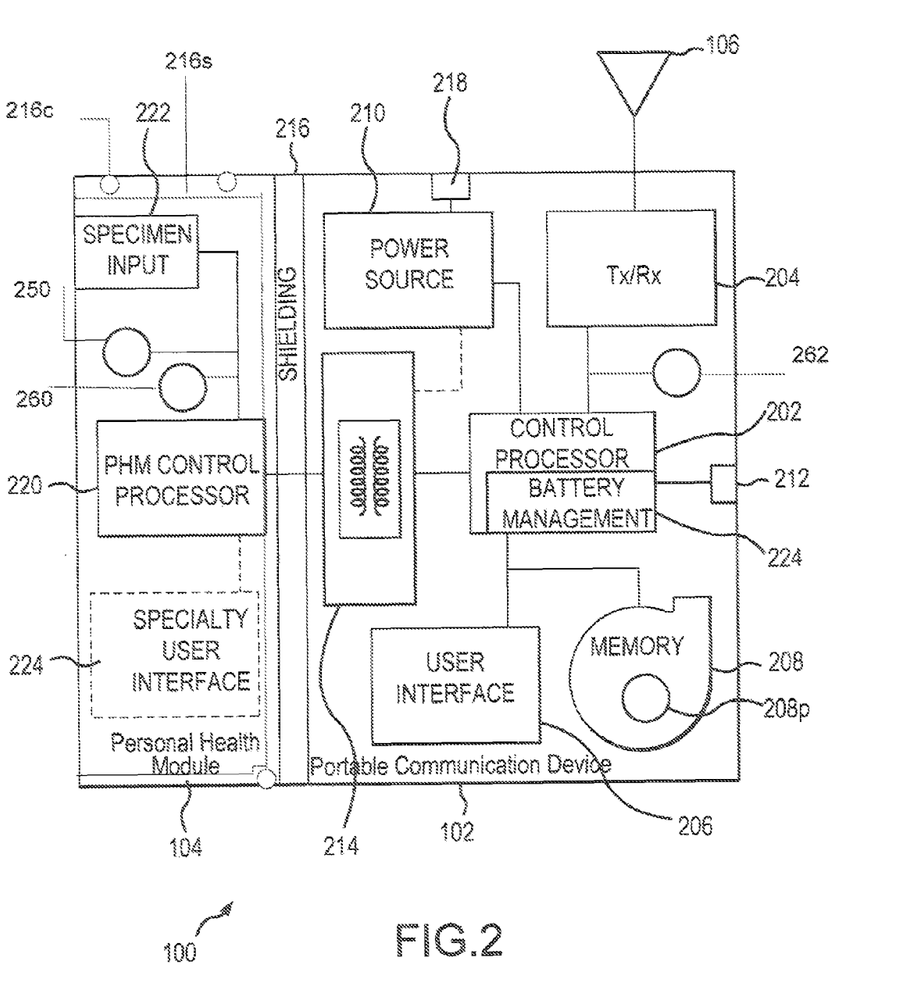
FIG. 2 is a functional block diagram of a wireless device of an exemplary embodiment.

Referring now to FIG. 2, a functional block diagram of portable communication device 102 and PHM 104 are shown in more detail in an exemplary embodiment. Portable communication device 102 includes several components including a control processor 202. Control processor 202 controls the major functions of portable communication device 102 including providing computing functionality to process the inputs and/or data required for the operation of portable communication device 102. Transmit/receive circuitry 204 is connected to control processor 202 and antenna(s) 106. Transmit/receive circuitry 204 may be one or more actual circuits and may work over various protocols and wavelengths. Transmit/receive circuitry 204 functions typical of such components as used in wireless communications, such as modulating signals received from the control processor 202 that are to be transmitted from antenna 106, and demodulating signals received at antenna 106. The demodulated signal is provided to control processor 202.

Portable communication device 102 includes a user interface 206. User interface 206 may comprise a user interface typical of a cellular phone or typical of the wireless device, such as, for example, a keyboard, alphanumeric pad, mouse, track ball, touch screen, voice recognition, microphones, speakers, data ports, input ports, or the like. Optionally, as in this exemplary embodiment, user interface 206 may include features typical of PHM 104. See U.S. patent application Ser. No. 11,682,755 titled WIRELESS DEVICE WITH PRIVACY SCREEN, filed Mar. 6, 2007, and identified by Attorney Docket Number IDF 060948. Alternatively, as described below, PHM 104 may have a separate user interface.

Portable communication device 102 includes a memory 208 connected to control processor 202. Memory 208 may store data and processing instructions necessary or convenient for operation of portable communication device 102. Memory 208 may include volatile and/or nonvolatile memory on any suitable media. Moreover, memory 208 may include a protected portion 208$p$ accessible only on entry of an authentication code, such as, for example, a password or biometric data. Moreover protected portion 208$p$ may be encrypted. Memory 208 may store data relating to information recorded by PHM 104 as well. For data contained in memory 208 relating to PHM 104, the data may be stored in memory 208 as if memory 208 was a primary store of data, a backup store of data for a memory contained in PHM 104 (not specifically shown), used to check data stored in primary memory, or the like.

Portable communication device 102 includes a power source 210. Power source 210 may be any conventional power source and is typically a battery pack. Power source 210 is connected to a recharge port 218 that is connectable to, for example, a wall socket, a car lighter, or the like. Portable communication device 102 also may include a data port 212 (data port 212 may sometimes be referred to as an input port 212 or an output port 212 depending on the context) connected to control processor 202. While not illustrated in FIG. 2, portable communication device 102 includes additional components and connections, such as, for example, cables, interfaces, circuit boards, and the like conventional in such devices for operation.

Portable communication device 102 includes an isolation circuit 214. Isolation circuit 214 will be explained further below but is to provide electrical isolation between portable communication device 102 and PHM 104 to inhibit failures or operations of portable communication device 102 from electrically interfering with PHM 104. Alternatively, isolation circuit 214 may be contained in PHM 104.

As explained above, wireless device 100 combines PHM 104 and portable communication device 102 in a connectable or integrated arrangement. PHM 104 may use certain components (such as a memory) of portable communication device 102 or may include separate components. For example, PHM 104 may include a PHM control processor 220 to control the major functions of PHM 104 including providing computing functionality to process the inputs and/or data required for the operation of PHM 104. For example, if PHM 104 was a blood glucose monitor, PHM 104 would have a specimen input 222, which as shown is a biological or test strip input so PHM 104 receives a blood sample. PHM control processor 220 would provide the control to identify blood glucose based on the specimen. Other PHMs 104 may be provided with specialty user interfaces 224 as needed. However, PHM 104 may provide and receive data over isolation circuit 214 to portable communication device user interface 206, which includes a display. This would be especially true if PHM 104 only required a user interface compatible with a conventional cellular telephone user interface, for example.

While PHM 104 may contain a separate power supply (not specifically shown), PHM 104 can receive power from power source 210. Power may be supplied over isolation circuit 214. While electrical isolation circuit 214 is helpful, wireless device 100 includes shielding 216, which may reside in portable communication device 102 or PHM 104. Shielding may be, for example, electromagnetic shielding to inhibit radio frequency transmissions from antenna 106 or other RF transmission components from interfering with the PHM 104 or the associated PHM control processor 220. Types of electromagnetic shielding are generally well known in the art and will not be further explained herein. Providing isolation circuit 214 and shielding for shielding 216 segregates portable communication device 102 and PHM 104. Thus, it is envisioned that while certain PHM 104 may be subject to regulation relating to medical devices from the United States Food and Drug Administration, portable communication device 102 may not be subject to the regulations due to the electrical, mechanical, and shielding isolation.

Moreover, shielding 216 may include heat shielding as is generally know in the art, such as, fiberglass insulation, phase change material insulations, or the like to regulate the temperature internal to PHM 104. Heat shielding may be necessary in some cases where PHM 104 requires operation in a controlled temperature (additional temperature precautions are described below). Heat shielding may be particularly useful as portable communication device may include electronic components that generate sufficient heat to impact the PHM 104 operation. Shielding 216 also may include sealing components 216s such as a gasket or o-ring to provide a moisture barrier to inhibit moisture from impacting PHM 104. Sealing components may include hermetic sealing components to reduce environmental impacts to PHM 104. Sealing components additionally may include antibacterial or anti microbial components 216c, which also may reduce the spread of infections.

Frequently, operation of PHM 104 is vital to a user's health while operation of remote station portion 102 is often a matter of convenience. Thus, if power source 210 supplies power to both PHM 104 and portable communication device 102, care must be taken to ensure sufficient power remains for operation of PHM 104, at least for a predetermined amount of time. To ensure sufficient power for PHM 104, control process 202 may have a battery management module 224. Battery management module 224 would monitor a charge on power source 210 and shut down functions of portable communication device 102 as charge dropped. For example, if system requirements are at predetermined charge, such as, for example, 50% full charge, only PHM 104 is powered to ensure PHM 104 has sufficient power for a predetermined amount of time. Thus, control processor 202 would such down all remaining functions of portable communication device 102. However, at higher charges, such as, for example, 60% of full charge, only certain functions of portable communication device 102 may be shut down. For example, at 60% charge internet functionality may be disabled or a Global Positioning System may be shut down, but cellular communication is maintained.

Figure 3:
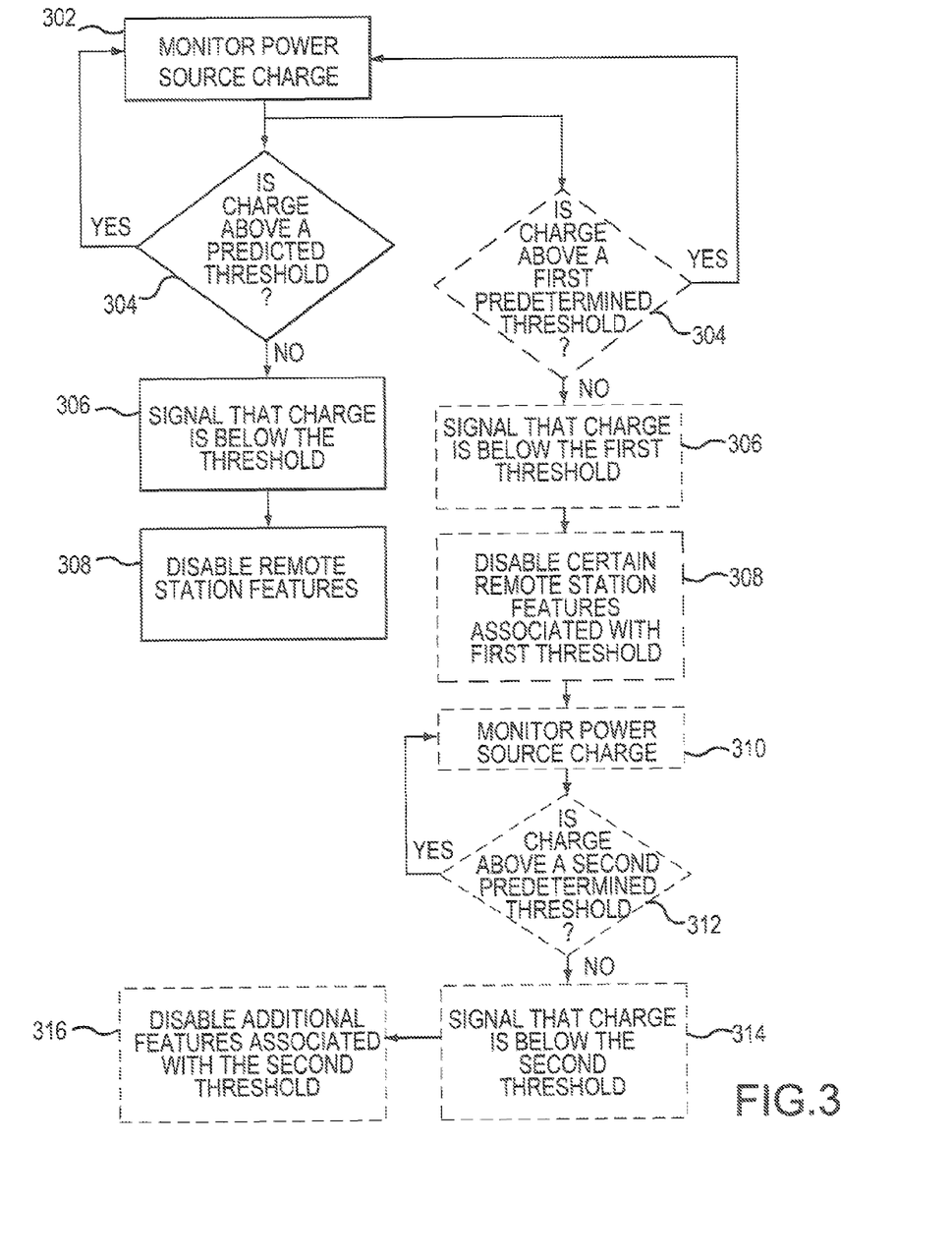
FIG. 3 is a flow chart diagram illustrating the operational steps of an exemplary embodiment.

Referring now to FIG. 3, a flow chart 300 showing an exemplary operation of battery module 224 is shown. First, battery management module 224 monitors a charge of power source 210, step 302. During operation of wireless device 100, battery management 224 determines whether the monitored charge of power source 210 is above a predetermined threshold, step 304. If charge is above a predetermined threshold, control reverts back to step 302 and steps 302 and 304 are repeated. If charge is below a predetermined threshold, battery management module 224 sends a signal to control processor 202 indicating charge is below the threshold, step 306. Control processor 202 disables or turns off features of portable communication device 102, step 308.

Control processor 202 could disable all features of portable communication device 102 based on a single comparison. Alternatively (as shown in phantom), battery management module at step 304 may determine whether charge is above a first predetermined threshold, step 304. If charge is below the first predetermined threshold, such as, for example, 75% full charge, battery management module would signal to control processor 202 that charge is below the first threshold, step 306. Control processor 202 would correspondingly disable or turn off a first series of functions associated with the first threshold, step 308. For example, control processor 202 may disable non-essential functions of remote station portion 102, such as, for example, internet connectivity, but maintain other functions of portable communication device 102, such as, for example, cellular communication.

Battery management module would continue to monitor charge subsequent to disabling of non-essential functions, step 310. Battery management module would determine whether charge drops below a second predetermined threshold, such as, for example, 30% full charge, step 312. If charge is determined not to be below 30% full charge, control returns to step 310 and steps 310 and 312 are repeated. If charge is determined to be below 30% full charge, battery management module signals control processor that charge is below the second predetermined threshold, step 314. Control processor would terminate a next series of functions associated with the second predetermined threshold, step 316. For example, control processor may disable a further series of non-essential functions for portable communication device 102 that are more essential than those previously disabled, but still not essential functions. Alternatively, the next series of functions may be the remaining essential functions. As one of ordinary skill in the art will now recognize on reading the disclosure, the number of thresholds and the associated functions that are disabled as power drops below a particular threshold are a matter of design choice and operational conditions.

Figure 4:
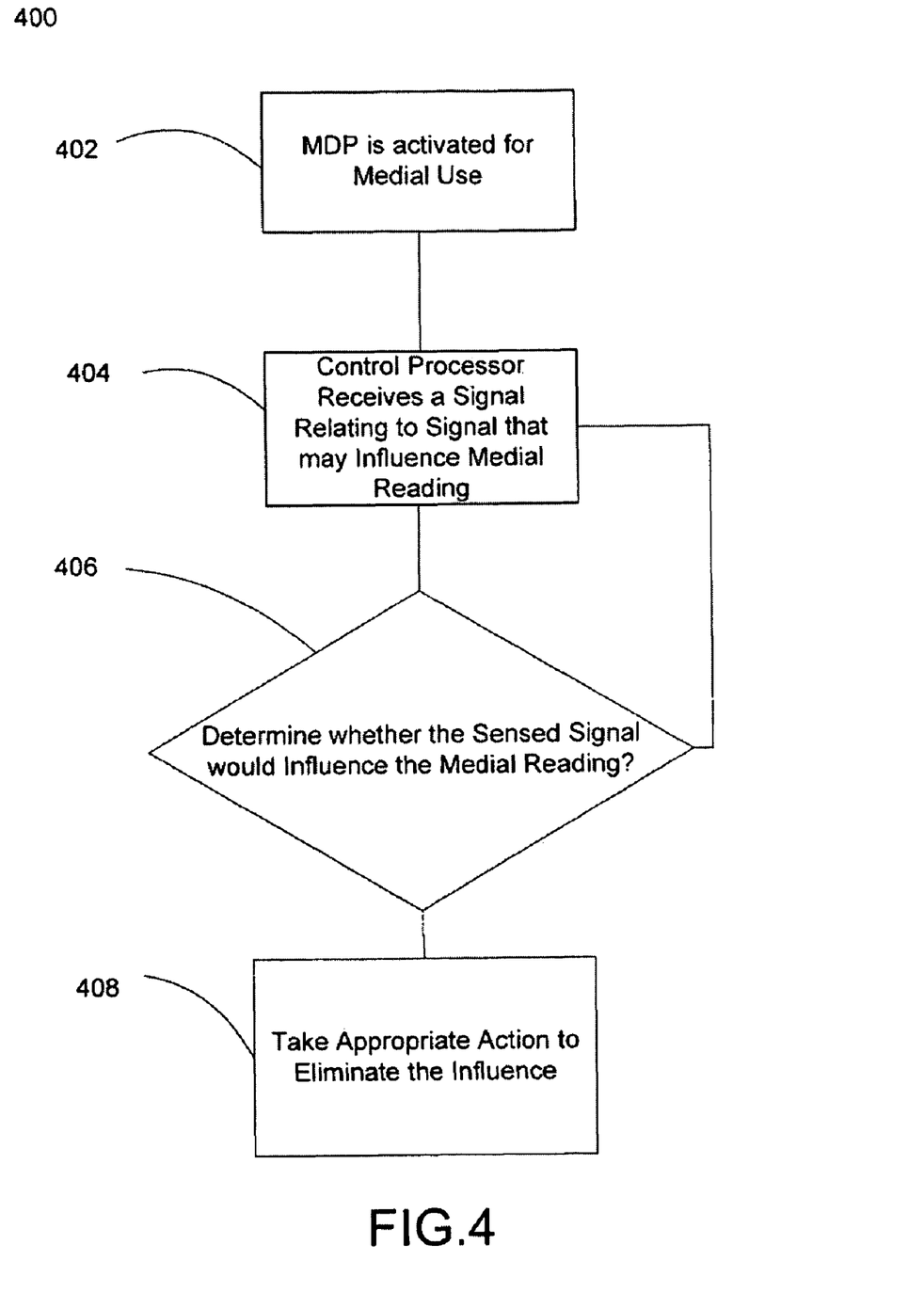
FIG. 4 is a flow chart diagram illustrating the operational steps of an exemplary embodiment.

As mentioned above, PHM 104 has particular operating characteristics that need to be preserved. Operation of PHM 104 may be influenced by operation of electronics such that radio frequency interferences causes malfunction of PHM 104 despite RF shielding installed on the device. Moreover, electronics typically have heat signatures. Many PHMs require biological and/or physiological readings to be taken within certain temperature ranges for accuracy. Thus, a sensor 250 may be provided in device 100. Sensor 250 may sense RF, temperature, moisture, biologics, or the like that may influence readings of PHM 104. As sensor 250 relates to operation of PHM 104, it is envisioned that sensor 250 would be contained in PHM 104, but it may be provided anywhere. Referring now to FIG. 4, an exemplary methodology using sensor 250 is provided. Sensor 250 may be used to as explained herein to control operating conditions of the wireless device such that the conditions of the wireless device remain within the operational range of PHM 104. First, optionally, PHM 104 is activated for a medical use, step 402. It is possible PHM 104 continuously monitors and or continuously reads biological and/or physiological conditions, it this case, step 402 is always potentially satisfied. Next, a control processor, which can be control processor 220 or 212, receives a signal from sensor 250 relating to a condition that may influence of operation of the medial use, step 404. In some cases, sensor 250 may continually send a signal regardless of whether PHM 104 is activated for medical use as the sensed condition may have a long change time, such as, for example, temperature. Sensor 250 may sense, for example, RF strength, temperature, moisture, etc. Based on sensor 250, control processor 220 or 202 determines whether a medical reading would be influenced by the RF strength, temperature, moisture or the like, step 406. In other words, at step 406 the control processor would determine whether the sensed condition is outside an operating range of the associated personal health module. If the sensor comparison indicates the sensed condition may influence the medical reading, appropriate action is taken to eliminate the influence, step 408. Typically, such actions include disabling components of the wireless device (either disabling portions of portable communication device 102 or portions of PHM 104). For example, powering off the radio frequency transmission circuits to reduce the radio frequency signal and powering on such circuits after the medial reading is completed. Another example may include powering off electronics to reduce a heat signature of the device to keep the device temperature within the required temperature range. Still other operations would depend on the operating specifics of the personal health module and the like. In some instances, the appropriate action may be displaying a warning to the user, such as, for example, displaying: "The environmental conditions are causing a high moisture reading that may influence the PHM 104, please relocate to a lower moisture environment if possible." For certain sensor information, such as, for example, temperature, the device may have multiple thresholds to turn off more and more electronics as the critical temperature is reached. Similarly, as temperature (or other sensor information) moves away from the critical temperature, the electronics or the like may be reinitiated. The thresholds for turning off and on electronics could be the same or be a hysterias type on/off loop where the electronics are turned off relatively close to the threshold, but not turned on until further from the threshold (or the opposite). In some cases, such as the RF signature, the electronics can be turned off, the reading taken, and turned back on. In some cases, such as temperature, the electronics may need to be turned off well in advance of the actual medical usage to avoid a situation where the reading cannot be taken due to the excessive temperature.

Figure 5:
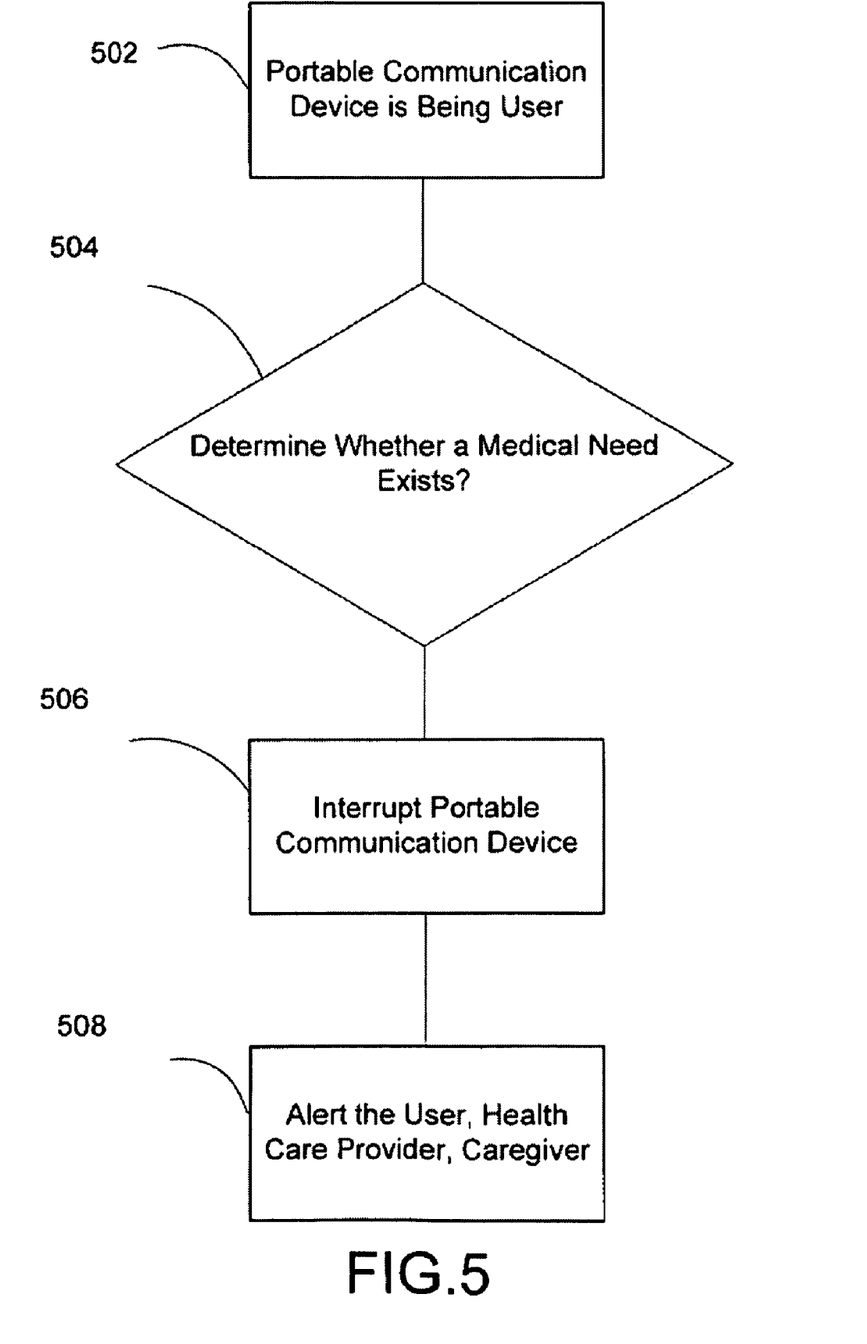
FIG. 5 is a flow chart diagram illustrating the operational steps of an exemplary embodiment.

In some cases, the user of wireless device 100 may be using portable communication device 102 for it's intended function, such as, for example, cellular communication, internet access, gaming, music playing or the like. While using the portable communication device 102, PHM 104 may receive or determine important health or medical information, such as, for example, it may detect an unexplained increase in heart rate, it may determine a blood pressure reading window is passing or pending. Thus, control processor 202 or 220, depending, may provide an interrupt signal alert the user to the medical need. FIG. 5 shows an exemplary flowchart 500 illustrative of a method interrupting based on medical need or information. First, at step 502, portable communication device is being used. Next, it is determined whether a medical need exists, is pending, or is passing, step 504. If it is determined a medical need exists, is pending, or is passing, the use of the portable communication device is interrupted, step 506. Optionally, the user could be alerted to the medical need, step 508. The interrupts may be preset by a provider, adjusted overtime, user provided or the like.

Referring back to FIG. 2, PHM 104 may contain a PHM clock 260. PHM clock 260 may operate as any conventional clock and will not be further explained herein. PHM 104 may require PHM clock 260 for any number of reasons including, for example, it is needed for one or more medical readings or the like. Portable communication device 102 frequently has a system clock 262. System clock 262 may be updated and maintained by a signal from a carrier. For example, cellular networks operating under CDMA protocols have precise clocks maintained at, for example, base stations that send clock information over the communication network to, for example, antenna 106 such that system clock 262 is updated by the precise clock (not shown in the figures). Thus, to provide more accurate PHM clock 260, system clock 262 may be coupled to PHM clock 260 via isolation circuit 214 such that system clock 262 (or more importantly, the precise network clock) is used to set, calibrate, or maintain PHM clock 260 in a conventional manner. The clocks 260 and 262 may be coupled via the control processors as shown, directly connected, or the like.

As mentioned above, PHM may have a stand alone memory, referred to herein as PHM memory. Conventionally, portable communication device also comprises a memory, such as the aforementioned memory 208, which may include protected memory 208p.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A wireless device comprising:
a portable communication device contained in a housing;
a control processor contained in the housing for controlling functions of at least the portable communication device;
a user interface connected to the control processor to allow a user to interact with at least the portable communication device;
transmit and receive circuits to provide modulation and demodulation of radio frequency signals between an antenna and the control processor;
a personal health module;
at least one isolation circuit electrically isolating the personal health module from the portable communication device of the wireless device and connecting the personal health module to at least the control processor and the user interface to monitor information relating to a patient;
shielding between the personal health module and the portable communication device to inhibit the portable communication device from impacting operation of the personal health device; and
a power source contained in the wireless device to provide power, wherein the personal health device is isolated from other components of the wireless device.

2. The wireless device of claim 1 wherein the personal health module is removably connected to the housing.

3. The wireless device of claim 2 wherein the removably connected personal health module is positioned such that the shielding reduces the effect of the portable communication device on the personal health module.

4. The wireless device of claim 1 wherein the personal health module further comprises a specialty user interface.

5. The wireless device of claim 1 wherein the control processor comprises a battery management module.

6. The wireless device of claim 5 wherein the battery management module monitors at least a charge on the power source, and the control processor disables at least one function of the portable communication device when monitored charge is below a predetermined threshold.

7. A wireless device of claim 6 wherein the at least one function comprises a plurality of functions and the plurality of functions are disabled based on at least two predetermined thresholds.

8. The wireless device of claim 1 wherein the shielding comprises electromagnetic shielding.

9. The wireless device of claim 1 wherein the shielding comprises heat shielding.

10. The wireless device of claim 1 wherein the shielding comprises at least one sealing component.

11. The wireless device of claim 10 wherein the at least one sealing component comprises a moisture barrier or a hermetic seal.

12. The wireless device of claim 11 wherein the at least one sealing component comprises at least one antimicrobial component.

13. The wireless device of claim 11, wherein the at least one sealing component comprises at least one antibacterial component.

14. A wireless device comprising:
means for housing a portable communication device, the portable communication device comprising at least a memory, a control processor, a user interface, a power source, and transmit/receive circuitry;
means for mechanically connecting a personal health module to the means for housing, the personal health module comprising at least a personal health module control processor;
means for electrically isolating the personal health module from the portable communication device; and
means for shielding the personal health module.

15. The wireless device of claim 14 wherein the personal health module uses and is electrically connected to the memory, the control processor, the user interface, the power source, and the transmit/receive circuitry of the portable communication device through the means for electrically isolating the personal health module from the portable communication device.

* * * * *